United States Patent [19]

Frey et al.

[11] Patent Number: 4,820,632
[45] Date of Patent: Apr. 11, 1989

[54] AGENT AND PROCESS FOR THE DETECTION OF REDOX SYSTEMS

[75] Inventors: Günter Frey, Ellerstadt; Gerd Zimmermann, Mannheim; both of Fed. Rep. of Germany

[73] Assignee: Boehringer Mannheim GmbH, Mannheim, Fed. Rep. of Germany

[21] Appl. No.: 774,353

[22] Filed: Sep. 10, 1985

[30] Foreign Application Priority Data

Sep. 15, 1984 [DE] Fed. Rep. of Germany ....... 3433946

[51] Int. Cl.$^4$ .......................................... G01N 21/78
[52] U.S. Cl. .......................................... 435/7; 435/16; 435/18; 435/24; 435/28; 436/63; 436/69; 436/111; 436/135; 558/166; 558/169; 558/170; 260/502.4 R; 260/502.5 D
[58] Field of Search ....................... 435/16, 18, 24, 28, 435/810, 7; 558/166, 169, 170; 260/502.4 R, 502.5 D; 436/63, 111, 135, 69

[56] References Cited

U.S. PATENT DOCUMENTS 4,492,754  1/1985  Trager .................................. 435/28
4,603,107  7/1986  Deneke ................................ 435/28

FOREIGN PATENT DOCUMENTS 44697    4/1970  Australia .
0007787  2/1980  European Pat. Off. .
0068356  1/1983  European Pat. Off. .
303734   7/1981  Fed. Rep. of Germany .

OTHER PUBLICATIONS

Chemical Abstracts 96: 22914K, (1982).
Chemical Abstracts 77: 75270m, (1972).
Chemical Abstracts 73: 25586r, (1970).
Chemical Abstracts 85: 33126d, (1976).
Chemical Abstracts 95: 36957t, (1981).
Chemical Abstracts 95: 23877s, (1981).
Chemical Abstracts 94: 217487q, (1981).
Chemical Abstracts 94: 216452n, (1981).
Tetrahedron, vol. 37, pp. 2297–2301, 1981.
Chemical Abstract 92: 146905v (1980).

(List continued on next page.)

Primary Examiner—Robert J. Warden
Assistant Examiner—Robert Benson
Attorney, Agent, or Firm—Felfe & Lynch

[57] ABSTRACT

The present invention is concerned with the use of aniline derivatives of the general formula:

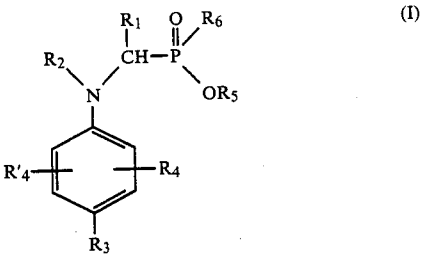

wherein $R_1$ is a hydrogen atom or a lower alkyl or aryl radical, $R_2$ is a hydrogen atom or a lower alkyl radical which can be substituted by hydroxyl, amino, carboxyl, lower alkoxycarbonyl, lower alkanoylamido, aryl lower alkyl or aryl or by a group of the structure:

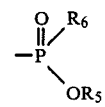

in which $R_5$ and $R_6$ have the meanings given hereinafter, $R_3$ is a hydrogen or halogen atom or a carboxyl group, $R_4$ and $R'_4$, which can be the same or different, are hydrogen or halogen atoms, carboxyl groups or lower alkoxy radicals or lower alkyl radicals which are preferably in the m-position and $R_1$ and $R_4$ or $R_2$ and $R_4$ or $R_4$ and $R'_4$, when the two substituents are ortho to one another, can together form a saturated or unsaturated hydrocarbon chain containing 2 to 6 carbon atoms which can be substituted by hydroxyl or oxo groups, $R_5$ is a hydrogen atom or a lower alkyl radical and $R_6$ is a hydroxyl group or a lower alkoxy, lower alkyl or aryl radical; and of the salts thereof with acids and bases (a) as colour former, together with an oxidisable coupling component, in the Trinder reaction for the detection of
   (a) hydrogen peroxide or hydrogen peroxide-forming systems or
   (b) peroxidase or peroxidate-acting substances or
(b) together with an oxidation agent for the detection of aromatic amines or of systems forming such amines.

The present invention also provides agents for the detection of redox systems containing the above aniline derivatives of general formula I.

Furthermore, the present invention provides new aniline derivatives coming within the ambit of the above general formula I, as well as processes for the preparation thereof.

8 Claims, 1 Drawing Sheet

OTHER PUBLICATIONS

Chemical Abstracts 101: 55192y (1984).
Stedman's Medical Dictionary, (p. 869), 24th Edition.
S. Hunig "Heterocyclic Azo Dyes by Oxidative Coupling", Angew. Chem. 70:215, (1958).
255th Edition, Clinical Dictionary Pschyrembel Klinisches Worterbuch, Walter de Gruyter, Berlin, New York 1986, p. 1663.
Methods of Enzymatic Analysis, (p. 222), 3rd Edition, vol. 1.
"Study of Various Substrates for Peroxidase-Coupled Peroxide Oxidations", Microchemcial Journ. 26:487, (1981).
Encyclopedia of Chemical Technology Kirk-Othmer, vol. 3, 3rd Edition, John Wiley and son, p. 392.
Fields, Journal of the American Chemical Society, 74(6), pp. 1528–1531, (1952).

AGENT AND PROCESS FOR THE DETECTION OF REDOX SYSTEMS

The present invention is concerned with reagents and processes for the detection of redox systems by the oxidative coupling of chromogens.

The detection of hydrogen peroxide by means of suitable chromogenic substances, catalysed by peroxidase or peroxidate-active substances, is of great importance not only for analytical chemistry but also for medical diagnosis. This applies especially for the numerous detection processes in which hydrogen peroxide is formed as an intermediate of the reaction of a substrate with the corresponding substrate oxidase and oxygen and subsequently, in the presence of suitable chromogenic substances and mainly in the presence of a peroxidase (POD) as catalyst, is converted into a compound which can be detected optically and has a quantitative relationship to the hydrogen peroxide formed. Furthermore, peroxidase is frequently used as an enzyme marker or label in immune tests and is detected by the addition of hydrogen peroxide and the above-mentioned chromogenic substances.

As examples, there may be mentioned the following compounds which, with the corresponding oxidases given in brackets, represent hydrogen peroxide-forming systems: glucose (glucose oxidase); galactose (galactose oxidase); L-amino acid (L-amino acid oxidase); cholesterol (cholesterol oxidase); uric acid (uricase); sarcosine (sarcosine oxidase); glycerol (glycerol oxidase); glycerol phosphate (glycerol phosphate oxidase); and pyruvate (pyruvate oxidase).

Numerous chromogens and indicator systems have already been described and used for the detection of hydrogen peroxide/peroxidase, one of the best known ones being the indicator system described by Trinder (Ann. Clin. Biochem., 6, 24–27/1969) in which phenol is oxidatively coupled with 4-aminoantipyrine in the presence of POD under the action of hydrogen peroxide to give a coloured material. Instead of phenol, as coupling component there can also be used phenol derivatives, naphthols, naphthol derivatives, aniline derivatives, naphthylamine, naphthylamine derivatives and substances which react in a similar manner. 4-Aminoantipyrine as coupling component can be replaced, for example, by aminoantipyrine derivatives, vanillin-diamine sulphonic acid, methylbenzthiazolinone hydrazone (MBTH) or sulphonated methylbenzthiazolinone hydrazone (SMBTH).

Furthermore, oxidative coupling is also used, for example, in order to determine aromatic amines liberated by enzymatic reactions. Of especial importance for diagnostic purposes are the detection of γ-glutamyl transpeptidase (γGT) and of leucine amino peptidase (LAP), as well as the detection of thrombin. In these cases, a "peptide amide", the amino acid sequence of which corresponds to the enzyme in question and the amide part of which is an aromatic amine, especially phenylenediamine or aminophenol or a derivative thereof, which can serve as coupling component of the reaction, is first split by the enzyme and then oxidised, using a phenol or aniline as coupling component, by means of an oxidation agent to give a coloured material (cf. Federal Republic of Germany Patent Specification No. 33 31 588 and European Patent Specification No. 0 076 042).

These detection reactions can be carried out not only in a cuvette but also on dry reagent carriers. The quantification thereof takes place by means of a photometer via a transmission measurement, by means of a remission photometer via a remission measurement or with the help of comparative colours by means of visual comparison.

In the literature, aniline derivatives have frequently been described with which there can be produced sensitive detection systems for hydrogen peroxide by condensation with 4-aminoantipyrine or substituted benzothiazolinone hydrazones (see Federal Republic of Germany Patent Specifications Nos. 28 33 612 and 30 37 342 and European Patent Specification No. 0 007 787). The coupling products thus produced display a high molar extinction coefficient which appears to be very well suited for the detection of corresponding hydrogen peroxide-forming compounds. However, a disadvantage thereof is the great tendency to disturbance of these coupling products due to serum components which give extinction differences of over 30% in comparison with pure aqueous solutions, as well as, in some cases, an insufficient stability of the compounds or of the coupling products.

Therefore, it is an object of the present invention to provide aniline derivatives which can be used as colour formers for oxidative couplings which are especially useful for the detection of hydrogen peroxide and of peroxidate-active substances and of aromatic, couplable amines which do not react with disturbing substances present in serum and which aniline derivatives are stable in weakly acidic to weakly alkaline ranges and thus can be used not only in cuvette tests but also in all matrices which can be used as dry reagent carriers.

Surprisingly, we have found certain aniline derivatives which fulfil the above-mentioned requirements.

Thus, the present invention is concerned with the use of aniline derivatives of the general formula:

(I)

wherein $R_1$ is a hydrogen atom or a lower alkyl or aryl radical, $R_2$ is a hydrogen atom or a lower alkyl radical which can be substituted by hydroxyl, amino, carboxyl, lower alkoxycarbonyl, lower alkanoylamido, aryl lower alkyl or aryl or by groups of the structure:

in which $R_5$ and $R_6$ have the meanings given hereinafter, $R_3$ is a hydrogen or halogen atom or a carboxyl group, $R_4$ and $R'_4$ are hydrogen or halogen atoms, carboxyl groups, lower alkoxy radicals or lower alkyl radicals which are preferably in the m-position and $R_1$ and $R_4$ or $R_2$ and $R_4$ and $R_4$ and $R'_4$, when the two substituents are ortho to one another, can together form a saturated or unsaturated hydrocarbon chain containing 2 to 6 carbon atoms which can be substituted by hydroxyl or oxo groups, $R_5$ is a hydrogen atoms or a lower alkyl radical and $R_6$ is a hydroxyl group or a lower alkoxy, lower alkyl or aryl radical, as well as the salts thereof with acids and bases, as colour formers in Trinder reactions, as well as with agents which contain these aniline derivatives.

The expression "lower alkyl" used herein means a straight-chained or branched alkyl radical containing up to 6 and preferably up to 3 carbon atoms, examples thereof including methyl, ethyl, isopropyl, isobutyl and tert.-butyl radicals.

The term "aryl" preferably means the phenyl radical, which can be additionally substituted by lower alkyl or alkoxy or halogen, and the naphthyl radical, which can possibly be partly hydrogenated.

Halogen includes fluorine, chlorine, bromine and iodine, fluorine and chlorine being preferred.

$R_1$ and $R_4$ or $R_2$ and $R_4$ or $R_4$ and $R'_4$ can together form a saturated or unsaturated hydrocarbon chain. Such a group can contain 2 to 6 and preferably 2 to 4 carbon atoms. Examples thereof include $-(CH_2)_2-$, $-(CH_2)_3-$, $-CH=CH-$, $-CH_2-CH=CH-$. Examples of saturated or unsaturated hydrocarbon chains substituted by hydroxyl or oxo groups include $-CH(OH)-(CH_2)_2-$ and $-CO-(CH_2)_2-CH=CH-CO-$.

Lower alkanoyl radicals are residues of carboxylic acids containing up to 6 carbon atoms, for example formyl, acetyl, propionyl, pivaloyl, isobutyryl.

Lower alkoxy radicals are radicals containing up to 6 and preferably up to 4 carbon atoms, for example methoxy, ethoxy, propoxy, isopropoxy and tert.-butoxy radicals.

The compounds of general formula I are, especially when $R_5$ is a lower alkyl radical and $R_6$ is a lower alkoxy radical, in part described, for example, in Zh. Obshch. Khim., 47, 2741/1977; Izv. Akad. Nauk SSSR, Ser. Khim., 424/1967 and 178/1982; U.S. Pat. No. 3,816,428; Z. Naturforsch., 36c, 242/1981; Chem. Abs., 99, 22914k; Chem. Abs, 91, 157812t; Bul. Soc. Chim. Fr. Pt., 2343/1979; Tetrahedron, 37, 2297/1981; J.A.C.S., 74, 1528/1952; and Czechoslovakian Patent Specification No. 190,240. The compounds there described are used, for example, as growth regulators for plants, as flotation adjuvants, as chelate formers and as corrosion inhibitors. The use thereof as components in oxidative coupling reactions for the colorimetric detection of hydrogen peroxide or of peroxidases or peroxidate-active compounds has hitherto not been described.

The present invention also provides new compounds of the general formula:

(I')

wherein $R_1$, $R_2$, $R_3$, $R_4$ and $R'_4$ have the same meanings as in formula I and $R'_6$ is a hydroxyl group or a lower alkyl or aryl radical, as well as the salts thereof with acids and bases and the preparation thereof by known methods.

The compounds of general formulae I and I' are stable and are either themselves readily soluble in water or, by reaction with conventional acids (mineral acids, such as hydrochloric acid, sulphuric acid, phosphoric acid and the like, or organic acids, such as acetic acid, citric acid, oxalic acid and the like) or with bases (aqueous solutions of sodium or potassium hydroxide, ammonia, amines, alkali metal carbonates and the like), can be converted into readily soluble salts.

The compounds of general formula I can be synthesised by known methods. A general summary of the possible reactions for the preparation of N—C—P—system is given in Topics in Phosphorus Chemistry, 8, 515 et seq./1976. In the following, there are given individual examples which are especially useful for the synthesis of compounds of general formula I:

1. As described, for example, in J.A.C.S., 74, 1528/1952, a primary or secondary amine can be reacted with an aldehyde and a dialkyl phosphite or a phosphonic acid dialkyl ester to give a compound of general formula I:

Instead of using a primary amine and an aldehyde as starting materials, there can also be used Schiff bases prepared therefrom.

2. N,O-acetals of general formula II, wherein $R_7$ is a lower alkyl radical, are reacted, with $H^+$ catalysis, with trialkyl phosphites of general formula III, in which $R_6$ is a lower alkoxy radical, to give phosphonic acid esters of general formula I, wherein $R_2$ is a hydrogen atom (see Izv. Akad. Nauk SSSR, Ser. Khim., 424/1967):

(II)     (III)

-continued

This reaction can also be carried out with phosphorous acid dialkyl esters (III, $R_6$=lower alkyl or aryl).

In the same way, cyclic N,O-acetals, for example N-aryloxazolidines (IV) can be reacted with trialkyl phosphites or phosphonic acid dialkyl esters. There can thereby be formed cyclic esters of phosphonic and phosphinic acid, especially when starting from oxazolidines, with intramolecular transesterification:

The N,O-acetals required as starting materials can be obtained, analogously to previously described reactions (J.A.C.S., 54, 4176/1932), by the reaction of secondary anilines with formaldehyde and alcohols. If N,N-dimethylanilines can be used as starting materials, then the corresponding N,O-acetals of formaldehyde can be prepared, as decribed in J.A.C.S., 31, 4058/1966, by anodic oxidation in methanolic potassium hydroxide solution. In the case of a correspondingly longer period of electrolysis, there can also be obtained bis-N,O-acetals of the general formula:

which can be reacted with 2 moles of trialkyl phosphite or phosphonic acid dialkyl ester to give the corresponding iminodimethanephosphonic acids.

Cyclc N,O-acetals can be prepared analogously to the open-chained compounds. Thus, for example, N-aryloxazolidines are obtained by the reaction of N-hydroxyethylanilines with aldehydes, for example formaldehyde.

3. Also known from the literature is the alkylation of anilines with phosphonic acid esters of general formula V, wherein X is bromine, iodine, tosyloxy, benzenesulphonyloxy or methanesulphonyloxy (J. Recherches, C.N.R.S., 119/1956; Zh. Obshch. Khim., 47, 2741/1977):

4. Aminoalkylphosphonic acid esters of general formula I, wherein $R_5$ is a lower alkyl radical, $R_6$ is a lower alkoxy radical and $R_1$ is preferably a hydrogen atom, can be metallised with strong bases, for example n-butyl lithium, on the α-carbon atoms and alkylated with alkylation agents, for example methyl iodide (Synthesis, 336/1977):

The compounds of general formula I, in which $R_5$ is a lower alkyl radical and $R_6$ is a lower alkyl or lower alkoxy radical, can be saponified by the action of concentrated mineral acids at boiling temperature, for example with hydrochloric acid, or by reaction with trimethylsilyl halides, especially trimethylsilyl bromide or iodide, and subsequent treatment with water. By treatment with sodium alcoholates or alkali metal salts, such as sodium iodide, from compounds of general formula I, in which $R_5$ is a lower alkyl radical and $R_6$ is a lower alkoxy radical, by means of known methods there can be prepared the corresponding phosphonic acid hemiesters.

The compounds of general formula I can be isolated in the form of the free bases or as salts of strong acids, for example hydrochloric, hydrogen tetrafluoroborate (HBF$_4$) or hydrobromic acid. When R$_5$ is a hydrogen atom, the compounds of general formula I can also be obtained as inner salts, alkali metal, ammonium or amine salts.

The aniline derivatives according to the present invention are normally present as inner salts since they contain not only acidic but also basic groups.

Those compounds which, in the 3-position to the amine nitrogen, contain an alkyl radical and especially a methyl radical are preferred since they display an increased extinction.

As coupling components capable of oxidation for the detection of hydrogen peroxide/POD, there are preferred 4-aminoantipyrine (4-AAP), 2-hydrazone-2,3-dihydro-3-methylbenzthiazolone (MBTH) and especially 2-hydrazono-2,3-dihydro-3-methylbenzthiazolone-6-sulphonic acid (SMBTH) but other compounds also known for their ability to undergo oxidative coupling can also be used in the same way.

For the detection of aromatic amines, i.e. especially of p-phenylenediamine and p-aminophenol derivatives, the aniline derivatives of general formula I also prove to be outstandingly useful since they are not susceptible to disturbance and, in the case of the oxidative coupling, give coloured materials of good stability and high extinction. Substrates which can be used for the detection of enzymes include compounds of the general formula:

(VI)

in which R''$_1$, R''$_2$, R''$_3$ and R''$_4$, which can be the same or different, are hydrogen or halogen atoms, alkyl and alkoxy radicals containing up to 6 carbon atoms, carboxyl or sulphonyl groups or R''$_1$ and R''$_2$ or R''$_3$ and R''$_4$ can also form an alkyl or alkylene bridge, X' is a hydroxyl group or an amino group, which can be substituted once or twice by alkyl and Y is an optionally protected amino acid or peptide group.

For the detection of leucylaminopeptidase, Y is L-leucyl, for the detection of γGT it is γ-L-glutamyl and for the detection of thrombin it is, for example, Tosyl—Gly—Pro—Arg.

As oxidation agent, apart from hydrogen peroxide/POD, there can also be used a peroxide, such as a persulphate or peracetate, as well as a periodate, Chloramine T and especially a cyanoferric complex, for example potassium ferricyanide. According to Federal Republic of Germany Patent Specification No. 33 31 588, oxidases can also be used.

As already mentioned, the system according to the present invention can be used for the detection of hydrogen peroxide and of hydrogen peroxide-producing systems, as well as of peroxidase and of peroxidate-active compounds. By hydrogen peroxide-producing systems, there are to be understood especially the substrate/substrate oxidase couples which are important in clinical diagnosis in which the substrate is oxidised in the presence of atmospheric oxygen, hydrogen peroxide being produced. Thus, in this way, it is possible to detect either substrate or the substrate oxidase, depending upon which component is added to the reagent. Furthermore, the compounds according to the present invention can be used for the detection of aromatic amines capable of coupling when they are brought into contact therewith in the presence of an oxidation agent. As examples, reference is made to the systems mentioned in the introduction hereto.

With the reagent combination, tests can be prepared which are measured in cuvettes. For this purpose, one of the compounds according to the present invention of general formula I is mixed together with the enzymes or other reagents necessary for the detection of a particular parameter, buffer, as well as possibly wetting agents, activators and other adjuvants as powder or pressed to form tablets or preferably dissolved in water and again dried or lyophilised. The reagent mixture thus obtained is, before use, dissolved in water or some other suitable solvent and the reagent solution thus prepared. After the admixture of the sample (substrate solution, enzyme solution, serum or plasma) with an aliquot of the reagent mixture, the resultant colour is measured on a photometer and the particular concentration or substrate concentration calculated via the molar extinction coefficients and the adder volumes of reagent or sample. Kinetic as well as end point measurements are possible.

In addition, the compounds of general formula I, in combination with the coupling partner capable of oxidation, together with peroxidase, the reagent(s) or other enzyme(s) required for the particular parameter detection, buffer system, possibly wetting agents and activators, as well as other adjuvants, can be impregnated into absorbent reagent carriers, such as papers, fleece or the like. For this purpose, one or more impregnation solutions can be prepared in the form of aqueous or organic or mixed solutions, depending upon how the reagents or adjuvants dissolve. Absorbent or swellable carriers, preferably filter paper or absorbent glass or synthetic resin fleece, are impregnated or sprayed with these solutions and subsequently dried. The reagent carriers thus prepared can be used either as rapid diagnostics for the direct determination of components of liquids (for example in body fluids), such as blood, urine or saliva or in foodstuffs, such as fruit juices, milk or the like). The liquid is thereby brought directly on to the reagent carrier or the reagent carrier can be briefly dipped into the liquid. A semiquantitative evaluation is possible by comparing the resultant colour with a comparison colour and a quantitative evaluation can be carried out by remission photometry. By elution of the above-mentioned reagents from the absorbent carrier with water, buffer or serum, a reagent solution can be prepared with which substrates or enzymes can be determined in the above-described manner in a cuvette, using a photometer. A quantitative determination by remission photometric evaluation can be carried out especially well when the indicator, together with the other necessary reagents and adjuvants and a film-forming synthetic resin is worked up to give a reagent film, for example according to Federal Republic of Germany Patent Specification No. 1,598,153. The smooth surface of such a film thereby gives less disturbances of the remission and a more homogeneous coloration than the absorbent papers usually employed.

Buffers used according to the present invention have a pH value of from 6 to 10 and especially of from 6.5 to 7.5. Phosphate, citrate, borate and GOOD buffers with alkali metal or ammonium counterions are most frequently used but other systems can also be employed.

Wetting agents are especially anionic and cationic wetting agents which enter into ionic exchange reactions with the zwitterionic compounds according to the present invention. However, non-ionic wetting agents which activate the enzymes can also be used. Sodium lauryl sulphate, dioctyl sodium sulphosuccinate and alkylaryl polyether alcohols are preferred.

As activators, there are used those which are known for the substrate reactions in question. The Trinder reaction itself is so rapid that an additional activation does not appear to be necessary.

As other adjuvants, it can be advisable to use conventional thickeners, emulsifiers, optical brighteners, contrast agents and the like, such as are known in corresponding tests with other chromogens.

The coupling reaction usually takes place at ambient temperature but can also readily be carried out at a higher temperature, for example at 37° C., if this is desirable for the reaction velocity of, for example, a preceding enzymatic reaction.

For the reactions with substrates or enzymes which usually occur, the following concentrations of the test solution have proved to be useful:

| | |
|---|---|
| aniline derivative | 0.05–100 mmol/l., preferably 0.1–1 mmol/l. |
| coupling component | 0.05–50 mmol/l., preferably 0.1–1 mmol/l. |
| buffer (pH 6–10) preferably pH 6.5–8 | 0.05–1 mol/l. preferably 0.1–0.5 mol/l. |
| wetting agent | 0–1.0 mol/l., preferably 0.05–0.1 mol/l. |
| a, peroxidase | 1.0–5000 KU/l. |
| b, $H_2O_2$ or $H_2O_2$— producing substrate/ enzyme mixture | 0.1–10 mmol/l. |
| other adjuvants | 0–5 mol/l. |

The above-given concentration ranges are to be so understood that the lower range is preferred for a photometric test in a cuvette and the upper range is preferred for rapid tests or tests on solid carriers.

For the detection of enzymes acting as amidases, in the above-given description, the coupling component is replaced by a corresponding amount of the peptide amide substrate and possibly instead of hydrogen peroxide there is used a corresponding amount of another oxidation agent.

The following Examples are given for the purpose of illustrating the present invention:

EXAMPLE 1.

1.1 A mixture of 21.4 g. N-methylaniline and 27.6 g. diethyl phosphite is mixed at 90° C. with 21.6 g. benzaldehyde, while stirring. The reaction mixture is kept for 1 hour at 90° C. and subsequently evaporated to dryness in a vacuum. The crude product is chromatographed over 1.5 liters of silica gel with ligroin/acetone (3:1 v/v). The fractions containing the product are concentrated and evaporated. There are obtained 25 g. (38% of theory) of oily α-(N-methylanilino)-benzylphosphonic acid diethyl ester. 1.2 3.3 g. α-(N-methylanilino)-benzylphosphonic acid diethyl ester are dissolved in 60 ml. dry methylene chloride and mixed dropwise with 7.92 ml. trimethylsilyl bromide. The reaction mixture is left to stand overnight and then evaporated to dryness. The residue is stirred with diethyl ether and 1.85 g. of crude product then filtered off with suction. This is dissolved in water and a little hydrochloric acid. The aqueous solution is extracted with diethyl ether, treated with activated charcoal and evaporated to dryness. The residue is triturated with diethyl ether and the precipitate is filtered off with suction and dried. There is obtained 1.1 g. (31% of theory) α-(N-methylanilino)-benzylphosphonic acid hydrobromide; m.p. 142°–146° C.

EXAMPLE 2.

2.1 71.6 g. N,N-dimethylaniline are dissolved in 800 ml. 2% methanolic potassium hydroxide solution and electrolysed at 1.5 A for 25 hours in a glass beaker. The anode consists of a platinum mesh (about 50 $cm^2$) and the cathode of a stainless steel mesh. The reaction solution is evaporated to dryness and the residue is taken up in diethyl ether. The insoluble residue is filtered off and the ether phase is evaporated. The remaining oil is distilled in a vacuum. After distilling twice through a Vigreux column, there are obtained 24.3 g. (27% of theory) N-methoxymethyl-N-methylaniline; b.p. 88.5°–89° C./7 mm.Hg. 2.2 5 ml. N-methoxymethyl-N-methylaniline and 4.6 ml. trimethyl phosphite are heated at 135° C. (bath temperature), while stirring, in a three-necked flask equipped with stirrer, dropping funnel and distillation bridge. 1.4 ml. acetic acid are added dropwise thereto portionwise in the course of 1 hour, the reaction mixture is further stirred for 1 hour and the reaction mixture then distilled in a high vacuum. There are obtained 4.4 g. (58% of theory) of oily (N-methylanilino)-methanephosphonic acid dimethyl ester; b.p. 126°–128° C./0.1 mm.Hg. 2.3 4.2 g. (N-methylanilino)-methanephosphonic acid dimethyl ester are boiled under reflux for 4 hours with 15 ml. concentrated hydrochloric acid. The reaction mixture is evaporated to dryness, the residue is dissolved in 10 ml. hot ethanol and the somewhat cooled mixed then mixed with diethyl ether. The precipitated crystals are filtered off with suction and dried. There are obtained 3.03 g. (78% of theory) (N-methylanilino)-methanephosphonic acid hydrochloride; m.p. 166°–168° C. (decomp.).

EXAMPLE 3.

The anilinophosphonic acids set out in the following Table 1 are prepared analogously to Example 2. The following Table 2 contains the N-methoxymethyl-N-methylanilines synthesised as starting materials and the following Table 3 sets out the anilinophosphonic acid esters prepared therefrom.

TABLE 1

| No. | $R_3$ | $R_4$ | m.p. °C. |
|---|---|---|---|
| 1 | H— | 3-Cl | 158–160° (decomp.) |
| 2 | H— | 3-$CH_3$ | 186–188° (decomp.) |
| 3* | H— | 3-$OCH_3$ | 128–129° HCl—free compound |
| 4 | F— | H— | 160–162° (decomp.) |
| 5 | F— | 3-$CH_3$ | 169–173° (decomp.) |

TABLE 1-continued $R_3$—[phenyl with $R_4$]—N(CH$_3$)(CH$_2$—P(OH)$_2$=O) × HCl

| No. | $R_3$ | $R_4$ | m.p. °C. |
|---|---|---|---|
| 6 | Cl— | H— | 140–143° (decomp.) |

*The compound is purified by chromatography over Dowex 50 in the H$^+$—form with water and recrystallised from isopropanol/water.

TABLE 2

$R_3$—[phenyl with $R_4$]—N(CH$_3$)(CH$_2$—OCH$_3$)

| No. | $R_3$ | $R_4$ | b.p. °C. |
|---|---|---|---|
| 1 | H— | 3-Cl | 98–103° (0.2 mm.Hg) |
| 2 | H— | 3-CH$_3$ | 80–81.5° (0.2 mm.Hg) |
| 3 | H— | 3-OCH$_3$ | 108–110° (0.2 mm.Hg) |
| 4 | F— | H— | 69–70° (0.15 mm.Hg) |
| 5 | F— | 3-CH$_3$ | 108–115° (0.15 mm.Hg) |
| 6 | Cl— | H— | 102–109° (1.3 mm.Hg) |

TABLE 3

$R_3$—[phenyl with $R_4$]—N(CH$_3$)(CH$_2$—P(OCH$_3$)$_2$=O)

| No. | $R_3$ | $R_4$ | b.p. °C. |
|---|---|---|---|
| 1 | H— | 3-Cl | 174–176° (0.3 mm.Hg) |
| 2 | H— | 3-CH$_3$ | 148–150° (0.2 mm.Hg) |
| 3 | H— | 3-OCH$_3$ | 176–177.5° (0.2 mm.Hg) |
| 4 | F— | H— | 145–147° (0.2 mm.Hg) |
| 5 | F— | 3-CH$_3$ | oily product* Rf-value 0.55 |
| 6 | Cl— | H— | 147–157° (0.2 mm.Hg) |

*purified by chromatography over silica gel, elution agent: ethyl acetate + 10% ethanol

EXAMPLE 4.

4.1 60.5 g. N-ethylaniline and 15 g. paraformaldehyde are dissolved in 100 ml. benzene and 50 ml. ethanol and boiled for 4 hours on a water separator. The solution is then evaporated to dryness and the residue is fractionally distilled. As main fraction, there are obtained 49.8 g. (56% of theory) N-ethyl-N-ethoxymethyl-aniline; b.p. 77°–80° C./0.1 mm.Hg 4.2 N-ethyl-N-ethoxymethylaniline is reacted with trimethyl phosphite analogously to Example 2.2. There is obtained an ester mixture which, besides the dimethyl phosphonic acid ester which is preponderantly present, also contains small amounts of diethyl and ethyl methyl ester due to transesterification; b.p. 139.5°–141.5° C./0.2 mm.Hg. By saponification with concentrated hydrochloric acid analogously to Example 2.3, there is obtained (N-ethylanilino)-methane-phosphonic acid hydrochloride; m.p. 105°–110° C. (decomp.).

EXAMPLE 5.

Analogously to Example 4, there are obtained the phosphonic acid (R=PO(OH)$_2$) set out in the following Table 4. Furthermore, Table 4 contains the alkoxymethylamines (R=—CH$_2$—O—Alkyl) prepared as intermediates and the phosphonic acid dialkyl esters (R=PO(O—Alkyl)$_2$) prepared therefrom. Individual phosphonic acid esters (cf. remarks in Table 4) are split with trimethylsilyl bromide analogously to Example 1.2. In the case of the preparation of compounds 3–8, triethyl phosphite is used.

TABLE 4

| No. | Structure | | physical data |
|---|---|---|---|
| 1 | indoline with N—CH$_2$—R | (a) R = —PO(OH)$_2$ hydrochloride | m.p.: 156° C. (decomp.) |
| | | (b) R = —PO(OCH$_3$)$_2$$^a$ | decomposition at T > 110° C. |
| | | (c) R = —OC$_2$H$_5$ | b.p.: 110–112° C. (0.1 mm.Hg) |
| 2 | 1,2,3,4-tetrahydroquinoline with N—CH$_2$—R | (a) R = —PO(OH)$_2$ hydrochloride | m.p.: 170–174° C. (decomp.) |
| | | (b) R = —PO(OCH$_3$)$_2$ | b.p.: 167–168° C. (0.2 mm.Hg) |
| | | (c) R = —OC$_2$H$_5$ | b.p.: 142–145° C. (4 mm.Hg) |
| 3 | PhN(CH$_2$Ph)(CH$_2$—R) | (a) R = —PO(OH)$_2$$^b$ | m.p.: 131–134° C. (decomp.) |
| | | (b) R = —PO(OC$_2$H$_5$)$_2$ | b.p.: 203–205° C. (0.3 mm.Hg) |
| | | (c) R = —OC$_2$H$_5$ | b.p.: 157–161° C. (0.4 mm.Hg) |
| 4 | PhN(CH$_2$—CH$_2$—CH$_3$)(CH$_2$—R) | (a) R = —PO(OH)$_2$ hydrochloride | m.p.: 72–75° C. (decomp.) |
| | | (b) R = —PO(OC$_2$H$_5$)$_2$ | b.p.: 142–146° C. (0.1 mm.Hg) |
| | | (c) R = —OC$_2$H$_5$ | b.p.: 94–100° C. (0.15 mm.Hg) |
| 5 | PhN(CH$_2$—CH$_2$—COOR')(CH$_2$—R) | (a) R = —PO(OH)$_2$, R' = H$^c$ | m.p.: 82–104° C. (decomp.) |
| | | (b) R = —PO(OH)$_2$, R' = C$_2$H$_5$$^c$ | m.p.: above 172° C. (decomp.) |
| | | (c) R = —PO(OC$_2$H$_5$)$_2$, R' = —C$_2$H$_5$ | b.p.: 176–178° C. (0.2 mm.Hg) |
| | | (d) R = —OC$_2$H$_5$, R' = —C$_2$H$_5$ | b.p.: 128–130° C. (0.2 mm.Hg) |

TABLE 4-continued

| No. | Structure | | physical data |
|---|---|---|---|
| 6 | ![structure 6] (4-F-C6H4)-N(C2H5)(CH2-R) | | |
| | (a) R = —PO(OH)2 | | m.p.: 135–138° C. (decomp.) |
| | (b) R = —PO(OC2H5)2 | | b.p.: 133–137° C. (0.15 mm.Hg) |
| | (c) R = —OC2H5 | | b.p.: 64–70° C. (0.15 mm.Hg) |
| 7 | N,N-diphenyl-N-CH2-R | | |
| | (a) R = —PO(OH)2[b] | | m.p.: 117–122° C. |
| | (b) R = —PO(OC2H5)2 | | b.p.: 183–187° C. (0.2 mm.Hg) |
| | (c) R = —OC2H5 | | b.p.: 133–135° C. (0.15 mm.Hg) |
| | 6-F-tetrahydroquinoline-N-CH2-R | | |
| | (a) R = —PO(OH)2 | | m.p.: 115–117° C. (decomp.) |
| | (b) R = —PO(OC2H5)2 | | b.p.: 165° C. (0.3 mm.Hg) |
| | (c) R = —OC2H5 | | b.p.: 103° C. (0.2 mm.Hg) |

[a] Purification by chromatography on silica gel elution agent: ethyl acetate + 2–10% ethanol
[b] This phosphoric acid is obtained from the corresponding dialkyl ester by splitting the ester with trimethylbromosilane (analogously to example 1.2)
[c] This phosphoric acid is purified by chromatography on the strongly acidic ion exchanger Dowex 50 H+—form with water as elution agent.

EXAMPLE 6.

Analogously to Example 2, from N,N-dimethyl-1-naphthylamine there is obtained the N-methoxymethyl compound which, by reaction with trimethyl phosphite, gives oily N-methyl-1-naphthylaminomethanephosphonic acid dimethyl ester which is purified by chromatography on silica gel with ligroin/acetone (3:1–3:2 v/v). Saponification of this ester by boiling with concentrated hydrochloric acid gives N-methyl-1-naphthylaminomethanephosphonic acid hydrochloride; m.p. 78°–80° C. (decomp.).

EXAMPLE 7.

7.1 18 g. 3-Phenyloxazolidine are reacted, analogously to Example 2.2, with trimethyl phosphite in the presence of glacial acetic acid. The crude product is purified by chromatography on silica gel with ligroin/ethanol (80:20–70:30 v/v). There are obtained 15 g. of an oily product which has the following structure:

7.2 2.3 g. of the compound obtained above are dissolved in 60 ml. dry methylene chloride and mixed, while stirring, with 7.9 ml. trimethylsilyl bromide. After standing overnight, the reaction mixture is mixed with 60 ml. concentrated ammonia solution. Stirring is continued for 1 hour, followed by evaporation to dryness. The residue is dissolved in ethanol, with the addition of concentrated hydrochloric acid. The solution is mixed with propylene oxide and the precipitate obtained is filtered off with suction. There are obtained 0.85 g. (40% of theory) N-(2-aminoethyl)-anilinomethanephosphonic acid; m.p. 280°–285° C. (decomp.).

EXAMPLE 8.

18.3 g. N-methylanilinomethanephosphonic acid dimethyl ester (obtained from Example 2.2) are dissolved in 100 ml. dry diethyl ether and cooled to −70° C. 54 ml. n-butyl lithium (15% in hexane) are added dropwise thereto under an atmosphere of nitrogen. The reaction mixture is stirred for 2 hours at −70° C., mixed with a solution of 4.9 ml. methyl iodide in 20 ml. diethyl ether, stirred for a further 2 hours at −70° C., left to stand overnight at ambient temperature and then shaken up with 20 ml. water. The organic phase is separated off, dried and evaporated. The remaining oil is chromatographed on silica gel with ethyl acetate/ethanol (98:2 v/v). There are obtained 21.5 g. of oily 1-(N-methylanilino)-ethanephosphonic acid dimethyl ester. This ester is split with trimethyl bromosilane analogously to Example 1.2. The crude product is chromatographed over silica gel with n-propanol/water/ammonia (6:3:1 v/v/v) as elution agent. The fractions containing the product are combined and, for the removal of the ammonium ions, are applied to the acidic ion exchanger Dowex 50 in H+ form. Elution with water and evaporation of the eluate gives 0.5 g. of a glassy product which, for purification, is recrystallised from acetone/diethyl ether. There is finally obtained 0.27 g. 1-(N-methylanilino)-ethanephosphonic acid; m.p. 103°–106° C. (decomp.).

EXAMPLE 9.

3.5 g. of the compound obtained in Example 7.1 are boiled under reflux for 5 hours with 25 ml. concentrated hydrochloric acid. The reaction mixture is evaporated and chromatographed over silica gel with n-propanol/water/ammonia (6:3:1 v/v/v) as elution agent. The fractions containing the product are combined and evaporated and the residue, for the removal of ammonium ions, is chromatographed over Dowex 50 in H+ form with water. After evaporation of the appropriate fractions, an oil remains behind which crystallises after several days. There is obtained 1.78 g. (50% of theory) N-hydroxyethylanilinomethanephosphonic acid; m.p. 120°–121° C.

EXAMPLE 10.

N,N-Bis-(methoxymethyl)-aniline is reacted, analogously to Example 2.2, with 2 mole trimethyl phosphite and the bis-phosphonic acid dimethyl ester obtained is saponified with trimethylsilyl bromide analogously to Example 1.2. For purification, the crude product is chromatographed over a strongly acidic ion exchanger (Dowex 50 in H+ form) with water. After evaporation of the fractions containing the product, there is obtained a glass which becomes crystalline after trituration with a mixture of acetone, diethyl ether and ligroin. There is obtained phenyliminodimethanephosphonic acid; m.p. 130°–131° C.

EXAMPLE 11.

11.1 Analogously to Example 2.2, 2.2 ml. methanephosphonic acid diethyl ester are reacted with 2 g. N-methoxymethyl-N-methylaniline at a bath temperature of 100° C. There is obtained 1.65 g. (55% of theory) [(N-methylanilino)-methyl]-methylphosphonic acid ethyl ester (b.p. 123° C./0.1 mm.Hg) which still contains a small amount of the corresponding methyl ester.

11.2 2 g. of the product obtained above are heated under reflux for 4 hours with 8 ml. concentrated hydrochloric acid. The mixture is evaporated to dryness and the residue is recrystallised from ethanol/diethyl ether. There is obtained 1.98 g. (95% of theory) [(N-methylanilino)-methyl]-methylphosphonic acid hydrochloride; m.p. 166°–168° C. (decomp.).

EXAMPLE 12. 4.5 g.

(N-methylanilino)-methanephosphonic acid dimethyl ester are dissolved in 20 ml. methyl ethyl ketone and mixed with 3 g. sodium iodide. The mixture is boiled under reflux for 30 minutes, cooled and mixed with diethyl ether. The precipitate obtained is filtered off and recrystallised from ethanol/diethyl ether. For further purification, the product is chromatographed over silica gel with ethanol as elution agent. The fractions containing the product are evaporated and the residue is recrystallised from ethanol/diethyl ether. There is obtained 0.71 g. (15% of theory) (N-methylanilino)-methanephosphonic acid monomethyl ester which decomposes upon heating above 180° C.

EXAMPLE 13.

1.5 g. (N-(2-aminoethyl)-anilino)-methane-phosphonic acid (from Example 7) are dissolved in 4 ml. water and 6 ml. 2N aqueous sodium hydroxide solution. The solution is mixed with a little glacial acetic acid until a turbidity occurs. Thereafter, 2 ml. acetic anhydride are added thereto, the mixture is stirred for 2 hours at ambient temperature and the solution then evaporated. The residue is chromatographed on 20 ml. Dowex 50 in H+-form with water. The fractions containing the product are combined and evaporated. The residue is recrystallised from ethanol/diethyl ether. There is obtained 1.25 g. (71% of theory) (N-(2-acetamidoethyl)-anilino)-methanephosphonic acid; m.p. 117°–118° C. (decomp.).

EXAMPLE 14.

14.1 19.85 g. Succinimide, 16.2 ml. aqueous 37% formaldehyde solution and 150 ml. ethanol are boiled under reflux for 45 minutes. The mixture is allowed to cool somewhat, a solution of 30.2 g. methyl 3-aminobenzoate in 50 ml. ethanol is added thereto and the reaction mixture is boiled under reflux for 6 hours. The reaction solution is evaporated somewhat and kept in a refrigerator. The precipitated crystals are filtered off with suction. There are obtained 33.4 g. methyl 3-succinimidomethylaminobenzoate which are dissolved in 90 ml. dimethyl sulphoxide and mixed with 4.75 g. sodium borohydride tablets. After the tablets have dissolved, the mixture is heated to 100° C. for 20 minutes. The mixture is then poured on to ice water and extracted with diethyl ether. The ethereal phase is mixed with a solution of 9 g. zinc chloride in 9 ml. water and vigorously stirred. The aqueous phase is separated off and the ethereal phase is washed with water. There are obtained 15.1 g. of oily methyl 3-N-methylaminobenzoate. 14.2 The above-obtained benzoic acid ester is reacted, analogously in Example 4.1, with paraformaldehyde and methanol to give the corresponding N,O-acetal which, analogously to Example 2.2, is reacted with trimethyl phosphite to give oily methyl 3-(N-dimethoxyphosphonomethyl-N-methyl)-benzoate which is purified by chromatography on silica gel with ethyl acetate/1% ethanol as elution agent. Saponification of this ester analogously to Example 2.3 gives 3-(N-dihydroxyphosphonomethyl-N-methyl)-benzoic acid; m.p. 189°–191° C. (decomp.).

EXAMPLE 15.

Determination of hydrogen peroxide in aqueous solution.

| Solution A: | 0.05 mmol/l. SMBTH[(1)] |
| --- | --- |
| | 0.5 mmol/l. aniline derivative |
| | 500 KU/l. peroxidase |
| | 0.1 mol/l. phosphate buffer (pH = 8.0) |
| Solution B: | 0.05 mmol/l. MBTH[(2)] |
| | 0.5 mmol/l. aniline derivative |
| | 500 KU/l. peroxidase |
| | 0.1 mol/l. phosphate buffer (pH = 8.0) |
| Solution C: | 0.05 mmol/l. 4-AAP[(3)] |
| | 0.5 mmol/l. aniline derivative |
| | 500 KU/l. peroxidase |
| | 0.1 mol/l. phosphate buffer (pH = 8.0) |

[(1)]3-methyl-2-benzthiazolinone hydrazone-6-sulphonic acid
[(2)]3-methyl-2-benzthiazolinone hydrazone
[(3)]4-aminoantipyrine 600 μl. phopsphate buffer (pH 8) are placed in a 1 cm. cuvette and, in each case, 100 μl. aniline derivative, peroxidase and coupler-containing solution added thereto. After adjustment of the blank value on an Eppendorf photometer, 100 μl. of a hydrogen peroxide stock solution ($c_{H_2O_2} \stackrel{\triangle}{=} 5 \times 10^{-5}$ mol/l.) are added thereto and, after 2 or 5 minutes, the extinction is measured at $\lambda_{max}$. The extinctions set out in the following Table 5 are determined, the aniline derivatives 8–10 being given for comparison. It can be seen that the anilinophosphonic acid derivatives of the present invention display extinctions which are 2 to 3 times higher than those of other acid group-containing anilines which had hitherto been used for the purpose according to the present invention.

TABLE 5

| aniline deriva- | SMBTH | | | MBTH | | | 4-AAP | | |
| --- | --- | --- | --- | --- | --- | --- | --- | --- | --- |
| tive* | $\lambda_{max}$ | 2' | 5' | $\lambda_{max}$ | 2' | 5' | $\lambda_{max}$ | 2' | 5' |
| 1 | | 1041 | | | 922 | | | 474 | |
| | 570 | | 1042 | 590 | | 932 | 560 | | 471 |
| 2 | | 1367 | | | 958 | | | 841 | |
| | 570 | | 1372 | 590 | | 962 | 550 | | 838 |
| 3 | | 911 | | | 973 | | | 294 | |
| | 560 | | 911 | 560 | | 972 | 550 | | 293 |
| 4 | | 1532 | | | 1412 | | | 544 | |
| | 560 | | 1516 | 560 | | 1435 | 550 | | 546 |
| 5 | | 1649 | | | 1307 | | | 790 | |
| | 570 | | 1656 | 580 | | 1319 | 560 | | 795 |
| 6 | | 918 | | | 912 | | | 175 | |

TABLE 5-continued

| aniline deriva-tive* | SMBTH $\lambda_{max}$ | 2' | 5' | MBTH $\lambda_{max}$ | 2' | 5' | 4-AAP $\lambda_{max}$ | 2' | 5' |
|---|---|---|---|---|---|---|---|---|---|
|  | 560 |  | 921 | 570 |  | 936 | 550 |  | 174 |
| 7 |  | 1823 |  |  | 1736 |  |  | 510 |  |
|  | 560 |  | 1822 | 570 |  | 1729 | 557 |  | 508 |
| 8 |  | 459 |  |  | 280 |  |  | 535 |  |
|  | 580 |  | 467 | 590 |  | 291 | 550 |  | 525 |
| 9 |  | 480 |  |  | 377 |  |  | 517 |  |
|  | 590 |  | 501 | 590 |  | 408 | 550 |  | 510 |
| 10 |  | 623 |  |  | 483 |  |  | 500 |  |
|  | 580 |  | 636 | 590 |  | 526 | 550 |  | 487 |
| 11 |  | 121 |  |  | 58 |  |  | 237 |  |
|  | 600 |  | 122 | 610 |  | 58 | 550 |  | 226 |
| 12 |  | 475 |  |  | 445 |  |  | 443 |  |
|  | 570 |  | 486 | 590 |  | 444 | 550 |  | 441 |

Designation of the aniline derivatives used.
1. (N—methylanilino)-methanephosphonic acid
2. (4-fluoro-N—methylanilino)-methanephosphonic acid
3. (3-methyl-N—methylanilino)-methanephosphonic acid
4. (4-fluoro-3-methyl-N—methylanilino)-methanephosphonic acid
5. (N—ethyl-4-fluoroanilino)-methanephosphonic acid
6. 1,2,3,4-tetrahydroquinolinyl-N—methanephosphonic acid
7. 6-fluoro-1,2,3,4-tetrahydroquinolinyl-N—methanephosphonic acid
8. (3-methyl-N—ethylanilino)-ethanesulphonic acid
9. 4-(N—ethyl-3-methylanilino)-methylbenzoic acid
10. sodium bis-(3-methylphenylimino)-propionate
11. 4-bis-(3-methylphenylimino)-methylbenzoic acid
12. N—hydroxyethyl-1,2,3,4-tetrahydroquinoline

EXAMPLE 16

Determination of serum disturbance

| Solution A: | 0.05 mmol/l. SMBTH[(1)] |
|---|---|
|  | 0.5 mmol/l. aniline derivative* |
|  | 500 KU/l. peroxidase |
|  | 0.1 mmol/l. phosphate buffer |
| Solution B: | 0.05 mmol/l. SMBTH[(1)] |
|  | 0.5 mmol/l. aniline derivative* |
|  | 500 KU/l. peroxidase |
|  | human serum |

*dissolved in phosphate buffer (0.1 mmol/l.; pH = 8.0)
[(1)]3-methyl-2-benzthiazolone hydrazone-6-sulphonic acid The extinction measurements are carried out with solution A as described in Example 15.

In the case of solution B, the 600 l. phosphate buffer present are replaced by human serum.

The extinction values obtained in both cases after 2 and 5 minutes are compared in the following Table 6:

TABLE 6

| aniline deriva-tive* | $\lambda_{max}$ | (mE) with SMBTH Puffer 2' | 5' | Serum 2' | 5' | Δ (mE) 2' | 5' | % |
|---|---|---|---|---|---|---|---|---|
| 1 | 570 | 1041 |  | 963 |  | −78 |  | 7.5 |
|  |  |  | 1042 |  | 961 |  | −81 | 7.8 |
| 2 | 570 | 1367 |  | 1150 |  | −217 |  | 15.8 |
|  |  |  | 1372 |  | 1146 |  | −226 | 16.5 |
| 3 | 560 | 911 |  | 895 |  | −16 |  | 1.8 |
|  |  |  | 911 |  | 898 |  | −13 | 1.4 |
| 4 | 560 | 1532 |  | 1287 |  | −245 |  | 16.0 |
|  |  |  | 1516 |  | 1281 |  | −235 | 15.5 |
| 6 | 560 | 918 |  | 808 |  | −110 |  | 12.0 |
|  |  |  | 921 |  | 802 |  | −119 | 12.9 |
| 7 | 560 | 1823 |  | 1545 |  | −278 |  | 15.2 |
|  |  |  | 1822 |  | 1558 |  | −264 | 14.5 |
| 8 | 580 | 459 |  | 127 |  | −332 |  | 72.2 |
|  |  |  | 467 |  | 131 |  | −336 | 71.5 |
| 9 | 590 | 480 |  | 168 |  | −312 |  | 65.0 |
|  |  |  | 501 |  | 190 |  | −311 | 62.2 |
| 10 | 580 | 623 |  | 404 |  | −219 |  | 35.3 |
|  |  |  | 636 |  | 413 |  | −223 | 34.8 |

*The aniline derivatives are set out hereinbefore.

EXAMPLE 17

Determination of triglycerides in serum

The reagents necessary for the detection are incorporated into a film coating mass:

| phosphate buffer (pH 8.0) | 0.2 mol/l. |
|---|---|
| detergent (fatty alcohol polyglycol ether) | 0.5% |
| SMBTH | 0.2 mmol/l. |
| (N—ethyl-4-fluoroanilino)-methane-phosphonic acid | 1 mmol/l. |
| glycerol phosphate oxidase | 1 KU/l. |
| glycerol kinase | 3 KU/l. |
| cholesterol esterase | 3 KU/l. |
| peroxidase | 10 KU/l. |

The coating mass is applied to a Pokalon film in a thickness of 200 μm. For film formation, the coated film is dried for about 30 minutes at 45° C. in a drying cabinet.

For the determination of the triglyceride concentration, 10 μl. of serum are applied to the film. After a reaction time of 2 to 3 minutes at 37° C., the remission is measured with a photometer. The triglyceride concentration can be calculated precisely by means of a previously produced calibration curve.

In the following Table 7, there are given the values for a calibration curve for the determination of the triglyceride concentrations:

TABLE 7

| concentration of triglycerides (mg/dl) | remission (%) |
|---|---|
| 100 | 64 |
| 150 | 52 |
| 200 | 41 |
| 250 | 33 |
| 300 | 27 |
| 400 | 22 |
| 500 | 18 |

EXAMPLE 18

Determination of creatinine in serum

Figure 1:
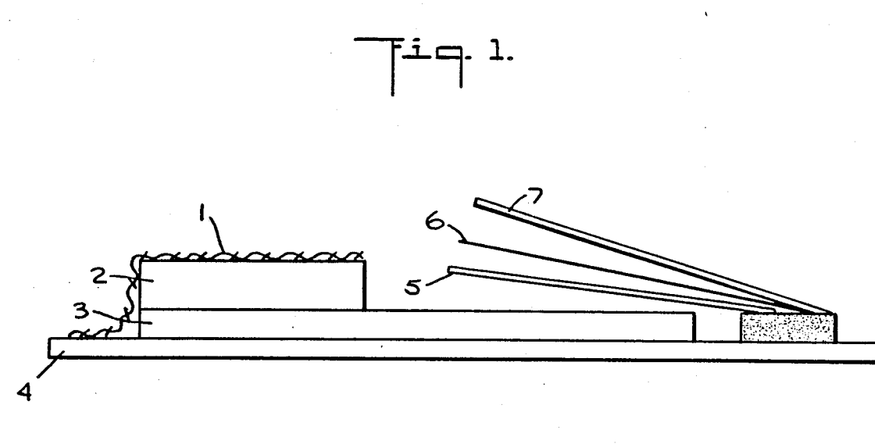

An absorbent carrier (for example stencil paper of the firm Schöller and Hösch; weight per unit surface area 12 g./m²; absorbency 50 ml./m²) is impregnated with a solution consisting of 20 mmol/l. 1,2,3,4-tetrahydroquinolinylmethanephosphonic acid and 300 KU/l. peroxidase dissolved in 0.2 molar phosphate buffer (pH 7.0) and dried (reagent paper A). Reagent paper B is prepared by impregnating the above paper with an impregnation solution consisting of 20 KU/l. sarcosine oxidase, 30 KU/l. creatinamidinohydrolase, 40 KU/l. creatinamidohydrolase and 100 mmol/l. sulphonated methylbenzthiazolinone hydrazone (SMBTH), as well as 0.1% detergent (fatty alcohol polyglycol ether) dissolved in 0.2 molar phosphate buffer (pH 8) and dried. For the detection of creatinine, the two reagent papers A and B are incorporated into the test device illustrated in FIG. 1 of the accompanying drawings in which the reference numerals have the following meanings:

1 = protective fabric
2 = separation zone
3 = transport zone
4 = carrier film
5 = reagent paper B
6 = reagent paper A -continued

| 7 = transparent covering film. |
|---|

For the detection of creatinine, 30 μl. of serum are pipetted on to the dosaging zone. The reaction is initiated by pressing the indicator and enzyme papers A and B on to the transport zone. After a reaction time of 1 minute at 37° C., the colour formed is measured remission photometrically. The creatinine concentration is determined via an appropriate calibration curve.

TABLE 8

Creatinine calibration curve

| serum creatinine (mg./dl.) | remission (%) |
|---|---|
| 0.5 | 59 |
| 1.0 | 50 |
| 1.5 | 42 |
| 2.0 | 35 |
| 5.0 | 22 |
| 10.0 | 15 |

EXAMPLE 19

Determination of the one-stage coagulation time according to Quick's method in a photometer 1200 μl. of a solution of the following composition are pipetted into a cuvette; 100 mol/l. tris/HCl buffer (pH 8.1), 6 mmol/l. calcium chloride, 0.1 mmol/l. Tos—Gly—Pro—Arg—p-phenylenediamine, 5 mmol/l. N-methyl-N-(4-methylphenyl)-methylenephosphonic acid and 1.2 mg./ml. rabbit brain thromboplastin. This solution is adjusted to a temperature of 37° C. 100 μl. citrate plasma and 100 μl. of an aqueous solution of 10 mol/l. potassium ferricyanide are simultaneously pipetted in, well mixed and, by means of a recorder started simultaneously with the addition of the sample, the increase of the extinction is monitored according to the time at a wavelength of 670 nm.

As measurement value, there is taken the time which expires from the start of the reaction up to the achievement of an extinction change of 0.1.

The function curve obtained according to the above-described process is set out in the following Table 9:

TABLE 9

| % Quick | seconds up to the achievement of an extinction change of 0.1 |
|---|---|
| 100% | 25.8 |
| 50% | 31.6 |
| 33% | 36.3 |
| 25% | 40.1 |
| 12.5% | 53.9 |
| 10% | 60.3 |

It will be understood that the specification and examples are illustrative but not limitative of the present invention and that other embodiments within the spirit and scope of the invention will suggest themselves to those skilled in the art.

What is claimed is:

1. A composition for the detection of hydrogen peroxide in the presence of peroxidase or peroxidatively reactive substances, wherein an aniline derivative and an oxidizable coupling compound are oxidatively coupled to form a colored compound, comprising,

(a) said oxidizable coupling compound and (b) said aniline derivative of the formula wherein $R_1$ is hydrogen, $C_1$-$C_6$ alkyl, $C_6$-$C_{10}$ aryl or $C_6$-$C_{10}$ aryl substituted by $C_1$-$C_6$ alkyl, $R_2$ is hydrogen, $C_1$-$C_6$ alkyl or $C_1$-$C_6$ alkyl substituted by hydroxyl, amino, carboxyl, lower alkoxycarbonyl, lower alkanoylamido, $C_6$-$C_{10}$ aryl substituted by $C_1$-$C_6$ alkyl or $C_6$-$C_{10}$ aryl or by a group of the structure:

in which $R_5$ is hydrogen or $C_1$-$C_6$ alkyl and $R_6$ is hydroxyl, $C_1$-$C_6$ alkoxy, $C_1$-$C_6$ alkyl, $C_6$-$C_{10}$ aryl or $C_6$-$C_{10}$ aryl substituted by $C_1$-$C_6$ alkyl;

$R_3$ is hydrogen, fluorine, chlorine, bromine, iodine or carboxyl;

$R_4$ and $R'_4$ which can be the same or different, are hydrogen, fluorine, chlorine, bromine, iodine, carboxyl, $C_1$-$C_6$ alkoxy or $C_1$-$C_6$ alkyl;

and the salts thereof with acids and bases.

2. The reagent of claim 1, wherein the oxidizable coupling compound is 4-aminoantipyrine or a derivative thereof or an unsulphonated or sulphonated methylbenzthiazolinone hydrazone.

3. In a method for the detection of hydrogen peroxide in the presence of peroxidase or of a peroxidatively reactive substance, comprising reaction of an aniline derivative and an oxidizable compound capable of oxidative coupling therewith, the improvement comprising using as aniline derivative a compound of formula I as defined in claim 1.

4. In a method for the detection an aniline compound comprising an oxidative coupling reaction between said aniline compound and a color former the improvement comprising using as color former an aniline derivative of formula I as defined in claim 1.

5. In a color-forming reagent for the detection of hydrogen peroxide or of peroxidase or of a peroxidatively reactive substance comprising an aniline derivative and an oxidizable compound capable of oxidative coupling therewith the improvement wherein it contains as aniline derivative a compound of formula I as described in claim 1.

6. A composition for the detection of an aniline compound, wherein said aniline compound is oxidatively coupled to a color former, comprising, (a) an oxidation agent, (b) a color former of the formula (I)

wherein $R_1$ is hydrogen, $C_1$–$C_6$ alkyl, $C_6$–$C_{10}$ aryl or $C_6$–$C_{10}$ aryl substituted by $C_1$–$C_6$ alkyl, $R_2$ is hydrogen, $C_1$–$C_6$ alkyl or $C_1$–$C_6$ alkyl substituted by hydroxyl, amino, carboxyl, lower alkioxycarbonyl, lower alkanoylamido, $C_6$–$C_{10}$ aryl substituted by $C_1$–$C_6$ alkyl or $C_6$–$C_{10}$ aryl, or by a group of the structure:

in which $R_5$ is hydrogen or $C_1$–$C_6$ alkyl and $R_6$ is hydroxyl, $C_1$–$C_6$ alkoxy, $C_1$–$C_6$ alkyl, $C_6$–$C_{10}$ aryl or $C_6$–$C_{10}$ aryl substituted by $C_1$–$C_6$ alkyl;

$R_3$ is hydrogen, fluorine, chlorine, bromine, iodine or carboxyl;

$R_4$ and $R'_4$ which can be the same or different, are hydrogen, fluorine, chlorine, bromine, iodine, carboxyl, $C_1$–$C_6$ alkoxy or $C_1$–$C_6$ alkyl;

and the salts thereof with acids and bases.

7. An agent for the determination of the, activity of blood coagulation factors comprising as a substrate for a blood coagulation factor Tos—Gly—Pro—Arg—p-phenylenediamine, buffer and potassium ferricyanide, and, as a chromogen capable of oxidatively coupling with the p-phenylenediamine liberated from said substrate by said coagulation factor, an aniline derivative of the formula (I)

wherein $R_1$ is hydrogen, $C_1$–$C_6$ alkyl, $C_6$–$C_{10}$ aryl or $C_6$–$C_{10}$ aryl substituted by $C_1$–$C_6$ alkyl, $R_2$ is hydrogen, $C_1$–$C_6$ alkyl or $C_1$–$C_6$ alkyl substituted by hydroxyl, amino, carboxyl, lower alkoxycarbonyl, lower alkanoylamido, $C_6$–$C_{10}$ aryl substituted by $C_1$–$C_6$ alkyl or $C_6$–$C_{10}$ aryl, by a group of the structure:

in which $R_5$ is hydrogen or $C_1$–$C_6$ alkyl and $R_6$ is hydroxyl, $C_1$–$C_6$ alkoxy, $C_1$–$C_6$ alkyl, $C_6$–$C_{10}$ aryl or $C_6$–$C_{10}$ aryl substituted by $C_1$–$C_6$ alkyl;

$R_3$ is hydrogen, fluorine, chlorine, bromine, iodine or carboxyl;

$R_4$ and $R'_4$ which can be the same or different, are hydrogen, fluorine, chlorine, bromine, iodine, carboxyl, $C_1$–$C_6$ alkoxy or $C_1$–$C_6$ alkyl;

and the salts thereof with acids and bases.

8. A composition for the detection of an enzyme comprising:

(a) a substrate of said enzyme of the formula in which $R_1''$, $R_2''$, $R_3''$ and $R_4''$ are independently hydrogen, fluorine, chlorine, bromine, $C_1$–$C_6$ alkyl, $C_1$–$C_6$ alkoxy, carboxyl or sulfo, or $R_1''$ and $R_2''$ or $R_3''$ and $R_4''$ together form a saturated or unsaturated hydrocarbon bridge of 3 or 4 carbon atoms; X' is hydroxyl, amino or amino substituted once or twice by $C_1$–$C_6$ alkyl; and Y is an unprotected or protected amino acid or peptide group;

(b) an oxidation agent and
(c) a compound of the formula I

I wherein $R_1$ is hydrogen, $C_1$–$C_6$ alkyl, $C_6$–$C_{10}$ aryl or $C_6$–$C_{10}$ aryl substituted by $C_1$–$C_6$ alkyl, $R_2$ is hydrogen, $C_1$–$C_6$ alkyl or $C_1$–$C_6$ alkyl substituted by hydroxyl, amino, carboxyl, lower alkoxycarbonyl, lower alkanoylamido, $C_6$–$C_{12}$ aryl substituted by $C_1$–$C_6$ alkyl or $C_6$–$C_{12}$ aryl, or by a group of the structure:

in which $R_5$ is hydrogen or $C_1$–$C_6$ alkyl and $R_6$ is hydroxyl, $C_1$–$C_6$ alkoxy, $C_1$–$C_6$ alkyl, $C_6$–$C_{10}$ aryl or $C_6$–$C_{10}$ aryl substituted by $C_1$–$C_6$ alkyl;

$R_3$ is hydrogen, fluorine, chlorine, bromine, iodine or carboxyl;

$R_4$ and $R'_4$ which can be the same or different, are hydrogen, fluorine, chlorine, bromine, iodine, carboxyl, $C_1$–$C_6$ alkoxy or $C_1$–$C_6$ alkyl; and the salts thereof with acids and bases.

* * * * *